United States Patent [19]
Perrine et al.

[11] Patent Number: 4,997,815
[45] Date of Patent: Mar. 5, 1991

[54] METHOD FOR AUGMENTING FETAL HEMOGLOBIN BY TREATMENT WITH ACTIVIN AND/OR INHIBIN

[75] Inventors: Susan P. Perrine, Richmond, Calif.; Norbert Albers, Hamburg, Fed. Rep. of Germany

[73] Assignees: Children's Hospital Medical Center of Northern California; Regents of the University of California, both of Oakland, Calif.

[21] Appl. No.: 266,421

[22] Filed: Nov. 1, 1988

[51] Int. Cl.$^5$ .................. A61K 37/38; A61K 37/43
[52] U.S. Cl. .......................................... 514/8; 514/12; 514/21; 435/7.25; 435/29; 435/184
[58] Field of Search ................ 514/8, 12, 21; 435/29, 435/184, 7

[56] References Cited

U.S. PATENT DOCUMENTS 4,740,587 4/1988 Ling et al. ............................ 530/313
4,822,821 4/1989 Perrine ................................. 514/557

FOREIGN PATENT DOCUMENTS 210461 2/1987 European Pat. Off. .
222491 5/1987 European Pat. Off. .

OTHER PUBLICATIONS

Kerlsson, *Annual Review*, Biochem. 54, 1071–108 (1985).
Schechter, *INSERM Symposium No. 9*, Rosa, Q., et al. (1979), Elsevier, pp. 129–137.
Perrine et al, *Biochem. Biophys. Research Comm.*, 148, 694 (1987).
Noguchi, et al., *New England J. Med.*, Jan. 14, 1988, 96–99.
Wood, et al., *British J. of Hematotogy*, 45, 431–445 (1980).
Perrine et al., Abstract, *The American Society of Hemotology 28th Annual Mtg.* (1986), "The Physiologic Metabolite Inhibits Fetal Hemoglobin Switching in Erythroid Progenitors of Neonates and HBSS Infants."
Marata et al., *PNAS USA* 85, 2434–2438 (1988).
Tsuji et al., *Biotechnology and Bioengineering* 31, 675–681 (1988).
Marata et al., *Biochem. and Biophys. Research Comm.* 151, No. 1, 230–235 (1988).
Shibata, et al., *Biochem. & Biophys. Research Comm.* 146, No. 1, 1987 (1987).
Yu, et al., *Nature*, 330, 24/31, 765–767 (Dec. 1987).
Eto, *Biochem & Biophys. Research Comm.* 142, No. 3, 1095–1103 (1987).

Primary Examiner—Howard E. Schain
Assistant Examiner—Choon P. Koh
Attorney, Agent, or Firm—Flehr, Hohbach, Test, Albritton & Herbert

[57] ABSTRACT

A method is provided for inhibiting the $\gamma$-globin to $\beta$-globin switching in subjects afflicted with $\beta$-globin disorders. The method is particularly adapted for ameliorating the clinical symptoms of sickle cell disease or $\beta$-thalassemias by periodically introducing into the subject prio r to natural completion of the switching process activin, inhibin, an inhibin chain or mixtures thereof.

49 Claims, No Drawings

METHOD FOR AUGMENTING FETAL HEMOGLOBIN BY TREATMENT WITH ACTIVIN AND/OR INHIBIN

The present invention is directed to a method for inhibiting or reversing the switching in in vivo or in vitro from production of γ to β-globin, thus augmenting the production of fetal hemoglobin. In particular, the present invention is directed to a method for controlling the fetal hemoglobin switch by introducing activin, inhibin or mixtures thereof to a mammal, or into erythroid cultures.

BACKGROUND OF THE INVENTION

Normal adult hemoglobin comprises a molecule with four polypeptide chains, two of which are designated α subunits and two of which are designated β subunits. Diseases known as sickle cell syndromes are associated with disorders in the β chain of the hemoglobin. However, in mammals, and particularly in humans, during fetal development, the fetus produces a fetal hemoglobin which comprises, instead of β-globin proteins, two γ-globin proteins. At some point during fetal development or infancy, depending on the particular species and individual, there is a so-called "globin switch" whereby the precursors of erythrocytes in the fetus switch from making predominantly γ-globin to making predominantly β-globin. It has been observed, however, that increased levels of fetal hemoglobin (derived from γ-globin) ameliorate the severity of sickling disorders. It has also been observed that subjects heterozygous for hereditary persistence of fetal hemoglobin syndromes (HPFH) and sickling hemoglobin (HbS) are clinically asymptomatic of sickle cell anemia. Also, infants with sickle cell anemia do not usually develop the symptoms of the disease until approximately four months of age when their fetal hemoglobin levels decrease. These observations suggest that a method for increasing the levels of fetal hemoglobin would be beneficial to patients with sickle cell syndromes.

It is thus an object of the present invention to provide a method for inhibiting or reversing the γ to β-globin switch in a fetus or infant to maintain increased fetal hemoglobin levels in those individuals with sickle cell syndromes and β-thalassemias.

Inhibin is a hormone which, among other effects, suppresses secretion of FSH (follicle-stimulating hormone) from the pituitary gland. Inhibin is a protein consisting of α and $\beta_A$ subunits linked by disulfide bonds. Activin, another hormone, sometimes also referred to as erythroid differentiation factor (EDF) or follicle-stimulating hormone releasing protein (FRP), is a homodimer consisting of either two $\beta_A$ subunits of inhibin (Activin A), two $\beta_B$ subunits of inhibin (Activin B), or a subunit each of $\beta_A$ and $\beta_B$ (Activin AB). These materials are present, in analogous forms, in mammals and have been reported, for instance, in human, porcine, and bovine follicular fluid. Porcine inhibin has been purified and sequenced from porcine follicular fluid as described in U.S. Pat. No. 4,740,587. The DNA encoding the prepro inhibin α and β chains of porcine or human inhibin has been isolated, ligated into expression vectors and expressed in mammalian culture See European Patent Application No. 222,491, published May 20, 1987. Activin A has been shown to induce hemoglobin accumulation in a human erythroleukaemic cell line and to induce the proliferation of erythroid progenitor cells in human bone marrow culture See Yu, et al., Nature, 330, 765 (Dec. 24, 1987). The structures and isolation of activin have been reported by several groups in the literature. See Vale, et al., Nature, 321: 776 (1986): Ling, et al., Nature, 321: 779 (1986); Ito, et al., Biochem. Biophys. Res. Comm., 142, 1095 (1987); Tsuji, et al., Biotech. Bioeno., 31, 675 (1988); Shibata, et al., Biochem. Biophys. Res. Comm., 146. 187 (1987). It has unexpectedly been found by the inventors herein that both activin and inhibin may inhibit or even reverse the γ to β-globin switch in a fetus or mammalian infant.

It is thus another object of the present invention to provide an agent for maintaining a high level of chain synthesis (thereby maintaining high fetal hemoglobin levels), without significant toxicity and long term side effects.

SUMMARY OF THE INVENTION

The present invention provides a method for ameliorating β-globin disorders in mammals comprising the step of introducing to a mammal a compound selected from the group consisting of activin, inhibin, an inhibin chain and mixtures thereof in an effective amount sufficient to inhibit or reverse fetal γ to β-globin switching. The method according to the present invention is particularly useful for ameliorating in humans the clinical effects of sickle cell disease. The invention additionally provides a diagnostic method for detecting sickle cell disease comprising the step of culturing a biological sample from a mammal with an effective amount of activin, inhibin, inhibin chain, or mixture thereof and measuring the decrease in β-globin synthesis in the culture as compared to a control.

DESCRIPTION OF THE INVENTION

The present invention provides a method for ameliorating the clinical effects of β-globin disorders, particularly the disorder of sickle cell anemia and β-thalassemias. The present invention is advantageous in that the compounds utilized may be physiologic factors, i.e., natural proteins found in the bloodstream of mammals and are thus, when introduced into a subject, are less likely to have toxic or undesirable long term side effects than a non-physiologic factor.

In accordance with the present invention, activin, inhibin, in any of their analogous mammalian forms, or mixtures of these are introduced to the subject (adult, fetus or infant) shown to or suspected of having a β-globin disorder, such as sickle cell disease or β-thalassemias.

As used herein, the term "biological sample" means any cells or body fluid from a mammal that can be diagnosed, including blood erythroid progenitors.

It is also intended that variants and single chains of activin or inhibin will be utilized alone or in mixtures with each other, or with activin and/or inhibin. By the terms "activin" and "inhibin" it is meant the dimers of α and β-chains of inhibin, prepro forms, and their prodomains, together with glycosylation and/or amino acid sequence variants thereof. The precursor may be used with or without the mature protein and, after cleavage from the mature protein, may be non-covalently associated with the mature protein. By the term "inhibin chain" it is meant to include, but not to be limited to, the α and β chains of inhibin, as well as their prepro forms and their prodomains, together with glycosylation and/or amino acid sequence variants of each chain thereof.

Generally, amino acid sequence variants will be substantially homologous with the relevant portion of the porcine or human α or β chain sequences set forth in the aforementioned European Patent Application 222,491, which is incorporated herein by reference in its entirety.

Substantially homologous means that greater than about 60% of the primary amino acid sequence of the homologous polypeptide corresponds to the sequence of the porcine or human chain when aligned in order to maximize the number of amino acid residue matches between the two proteins. Alignment to maximize matches of residue includes shifting the amino and/or carboxyl terminus, introducing gaps as required and/or deleting residues present as inserts in the candidate. Typically, amino acid sequences variants will be greater than about 70% homologous with the corresponding native sequences.

Variants that are not hormonally-active fall within the scope of this invention, and include polypeptides that may or may not be substantially homologous with either a mature inhibin chain or prodomain sequence, but which are (1) immunologically cross-reactive with antibodies raised against the native counterpart or (2) capable of competing with such native counterpart polypeptides for cell surface receptor binding Hormonally inactive variants are produced by the recombinant or organic synthetic production of fragments, in particular the isolated β chains of inhibin, or by introducing amino acid sequence variations so that the molecules no longer demonstrate hormonal activity as defined above.

Immunological or receptor cross-reactivity means that the candidate polypeptide is capable of competitively inhibiting the binding of the hormonally-active analogue to its receptor and/or to polyclonal antisera raised against the hormonally-active analogue. Such antisera are prepared in conventional fashion by injecting goats or rabbits S.C. with the hormonally-active analogue or derivative in complete Freunds adjuvant, followed by booster intraperitoneal or S.C. injections in incomplete Freunds.

The variants of inhibin include the pro and/or prepro sequences of the inhibin α or β chain precursors, or their immunologically or biologically active fragments, substantially free of the corresponding mature inhibin chains. The sequences for porcine and human inhibin are known, for example, as published in European Patent Application 222,491. The prepro sequence for the porcine α subunit precursor is the polypeptide comprised by residues 1 to about 230, while the $\beta_A$ subunit pro sequence is comprised by residues 1 to about 308. These sequences encompass prodomain sequences.

The intact isolated prepro or prodomain $\beta_A$, $\beta_B$ or α sequences are best synthesized in recombinant cell culture and the individual subcomponent domains are synthesized by routine methods of organic chemistry or by recombinant cell culture, for example as described in European Patent Application 222,491.

While the site for introducing a sequence variation is predetermined, it is unnecessary that the mutation per se be predetermined. For example, in order to optimize the performance of mutation at a given site, random mutagenesis may be conducted at the target codon or region and the expressed inhibin mutants screened for the optimal combination of desired activity. Techniques for making substitution mutations at predetermined sites in DNA having a known sequence are well known, for example M13 primer mutagenesis.

Mutagenesis is conducted by making amino acid insertions, usually on the order of about from 1 to 10 amino acid residues, or deletions of about from 1 to 30 residues. Substitutions, deletions, insertions or any subcombination may be combined to arrive at a final construct. Preferably, however, only substitution mutagenesis is conducted. Obviously, the mutations in the encoding DNA must not place the sequence out of reading frame and preferably will not create complementary regions that could produce secondary mRNA structure.

Covalent modifications of inhibin, activin or prodomains are included within the scope hereof and include covalent or aggregative conjugates with other chemical moieties. Covalent derivatives are prepared by linkage of functionalities to groups which are found in the inhibin amino acid side chains or at the N- or C-termini, by means known in the art. For example, these derivatives will include: aliphatic esters or amides of the carboxyl terminus or residues containing carboxyl side chains, e.g., aspartyl residues; O-acyl derivatives of hydroxyl group-containing residues such as seryl or alanyl; and N-acyl derivatives of the amino terminal amino acid or amino-group containing residues, e.g. lysine or arginine. The acyl group is selected from the group of alkyl-moieties (including C3 to C10 normal alkyl), thereby forming alkanoyl species, and carbocyclic or heterocyclic compounds, thereby forming aroyl species. The reactive groups preferably are difunctional compounds known per se for use in cross-linking proteins to insoluble matrices through reactive side groups, e.g. m-Maleimidobenzoyl-N-hydroxy succinimide ester. Preferred derivatization sites are at histidine residues.

The method used to introduce the compound will be any convenient method normally used to introduce pharmaceuticals into the bloodstream, such as by injection, bolus, infusion, and the like. Parenteral administration may also be utilized.

The exact size of an effective dose of a compound according to the method of the present invention will depend on a number of factors, including the particular recipient and the severity of condition; thus the route of administration will be ultimately at the discretion of the attendant physician.

While it is possible to utilize the compounds in vivo per se, it is preferable to present them as a pharmaceutical formulation preparation. The formulation of the present invention comprises a compound as previously described together with one or more acceptable carriers therefor and, optionally other therapeutic ingredients. The carriers must be acceptable in the sense of being compatible with other ingredients of the formulation and not deleterious to the recipient.

The Activin B is administered to the patient by any suitable technique, including parenteral, sublingual, topical, intrapulmonary, and intranasal administration. The specific route of administration will depend, e.g., on the type of therapy required. Examples of parenteral administration include intramuscular, subcutaneous, intravenous, intraarterial, and intraperitoneal administration.

The compositions to be used in the therapy will be formulated and dosed in a fashion consistent with good medical practice taking into account the clinical condition of the individual patient, the cause of the condition in need of therapy, the site of delivery of the composition, the method of administration, the scheduling of administration, and other factors known to practitioners. The "effective amount" for purposes herein is thus determined by such considerations.

As a general proposition, the total pharmaceutically effective amount of the activin and/or inhibin administered parenterally per dose will be in the range of about 50 μg/kg/day to 10 mg/kg/day of patient body weight, although, as noted above, this will be subject to a great deal of therapeutic discretion. The key factor in selecting an appropriate dose is the result obtained, as measured by inhibition of fetal γ-globin to β-globin switching or by other criteria as deemed appropriate by the practitioner.

The composition herein is also suitably administered by sustained release systems. Suitable examples of sustained release compositions include semi-permeable polymer matrices in the form of shaped articles, e.g., films, or microcapsules. Sustained release matrices include polylactides (U.S. Pat. No. 3,773,919, EP 58,481), copolymers of L-glutamic acid and gamma-ethyl-L-glutamate (U. Sidman, et al., *Biopolymers*, 22, 547-556 (1983)), poly(2-hydroxyethyl methacrylate) (R. Langer, et al., *J. Biomed. Mater. Res.*, 15: 167-277 (1981), and R. Langer, *Chem. Tech.* 12:: 98-105 (1982)), ethylene Vinyl acetate (R. Langer, et al., Id.) or poly-D-(—)-3-hydroxybutyric acid (EP 133,988). Sustained release compositions also include liposomally entrapped activin or inhibin or a mixture thereof. Such compositions are prepared by methods known per se: DE 3,218,121; Epstein, et al., *Proc. Natl. Acad. Sci. U.S.A.*, 82: 3688-3692 (1985); Hwang, et al., *Proc. Natl. Acad. Sci. U.S.A.* 77: 4030-4034; EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapy.

For parenteral administration, the activin or inhibin is formulated generally by mixing it at the desired degree of purity, in a unit dosage injectable form (solution, suspension, or emulsion) with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the activin or inhibin uniformly and intimately with liquid carriers or finely divided solid carriers or both and then, if necessary, shaping the product into the desired formulation. Preferably the carrier is a parenteral carrier, more preferably a solution that is isotonic with the blood of the recipient. Examples of such carrier vehicles include water, saline, Ringer's solution, dextrose solution, and 5% human serum albumin. Nonaqueous vehicles such as fixed oils and ethyl oleate are also useful herein, as well as liposomes. Generally, the carrier can contain minor amounts of additives such as substances that enhance isotonicity and chemical stability, e.g., buffers and preservatives, as well as low molecular weight (less than about 10 residues) polypeptides, proteins, amino acids, carbohydrates including glucose or dextrans, chelating agents such as EDTA, or other excipients. The activin or inhibin is typically formulated into such vehicles at a concentration of about 10 μg/ml to 100 μg/ml at physiological pH.

Activin or inhibin for use in therapeutic administration must be sterile. Sterility is readily accomplished by sterile filtration through (e.g., 0.2 micron) membranes. Activin ordinarily will be stored in unit or multidose containers, for example, sealed ampoules or vials, as an aqueous solution, as it is highly stable to thermal and oxidative denaturation. Lyophilized formulations for reconstitution are also acceptable.

Preferred unit dosage formulations are those containing a daily dose or a unit daily subdose, or an appropriate fraction thereof.

Alternatively, FSH (follicle-stimulating hormone) may be administered to stimulate in vivo inhibin and activin production within the subject or a pregnant subject for the treatment of a fetus. When treating a fetus, both with activin, inhibin or FSH, treatment should be administered to the fetus beginning at a time just prior to and during the time when the γ to β-globin switch occurs in the fetus. In humans, treatment typically will begin prior to the thirty-second week of gestation. When treatment by administering FSH is desired, treatment should be approximately 10-500 micrograms/kg body weight/every 2-8 hours for a period of 1 to 10 days just prior to and during the expected occurrence of the γ to β-globin switch. If activin and/or inhibin is given concurrently with FSH, the amount of FSH administered will usually be less than the above dosages.

As further application of the compounds according to the present method, they may be added in vitro to cell cultures taken from patients and the amount of β-globin synthesis measured to determine the potential efficacy of further treatment for the β-globin disorders, such as sickle cell disease. The compounds may be thus used in vitro in cell cultures from patients to determine whether further addition of one of the compounds would result in continued inhibition or reversal of the globin switch.

The frequency and dosages of administration of the above compounds will depend upon when the compound is introduced, whether the subject is a fetus, infant or adult, the size and weight of the subject, the condition of the patient, and the like. Generally, injections of activin and/or inhibin beginning at a dosage of about 50 μg/kg-10 mg/kg; and often as low as 50 μg/kg-100 μg/kg body weight per day during gestation, particularly prior to the thirty-second week of gestation in humans, will delay the γ to β switching. Dosages, up to about 10 mg/kg/day may be utilized at the discretion of the physician. Since apparently the switching process is not complete in humans until approximately four months after birth, treatment may be initiated after birth up until about the fourth month of infancy and continued as long as necessary to maintain enhanced fetal hemoglobin levels in the patient, or treatment may be initiated later in childhood or adulthood.

Treatment of infants preferably occurs prior to the fourth month of infancy since the γ to β switching process is difficult to reverse. Although treatment with one of the above compounds prior to the fourth month of infancy will inhibit the γ to β-switching process, treatment subsequent to that period may also achieve the desired clinical results, i.e., the amelioration of the effects of the β-globin disorder. Therefore, if the switching process is inhibited or reversed even to the extent of 10 to 20% (that is, the subject makes 10 to 20% more γ-globin than would be expected if the switch were allowed to occur), this may be sufficient to ameliorate the symptoms of the disease.

The method according to the present invention may be utilized in vivo, or in vitro as a diagnostic test by measuring the decrease in $\beta$-globin synthesis in the culture as compared to a control sample cultured for sickle cell disease in absence of the activin, inhibin, or inhibin chain. For the in vitro test erythroid cultures, such as that obtained from cord blood mononuclear cells in Iscove's Modified Dulbcco's Medium with 0.9% methylcellulose, may be used as described by Stamatoyannopoulous et al., Blood, 54, 440–450 (1979) and Friedman et al., J. Clin. Invest., 75, 1359-1368 (1985).

The following examples are provided by way of illustration, however, the invention is not intended to be limited in any manner thereby. Globin production, analyzed by electrophoresis on Tritonurea gels, autoradiography, and densitometry and by radioligand immunoassay of the total and fetal hemoglobin in pg per Bfu-e-derived cell, was performed as described in Stamatoyannopoulous et al. and Friedman et al., ibid. All citations in the examples are expressly incorporated herein by reference.

EXAMPLE 1

The $\gamma$-globin to $\beta$-globin switch (fetal to adult switch) in the sheep fetus occurs between 120 to 140 days of gestation, where a full gestation term is from 140 to 150 days. Ovine FSH was administered in a pulsatile fashion 5 micrograms every 3 hours for 5 to 10 days, to 9 catheterized ovine fetuses of 113 to 125 days of gestation. This increases gonadal inhibin production. Globin synthesis was assayed in ovine erythrocytes after tritium-leucine labeling by column chromatography before initiation of treatment and after day 5 and day 10 of administration. It was found that $\beta$-globin synthesis was decreased significantly from 82.1±8.8% of non-$\alpha$-globin in age-matched controls to 40.0±8.1% in FSH-treated fetuses between 132 and 140 days of gestation (P<0.001, n=8). One fetus had no detectable $\beta$-globin at 123 days gestation, more than 4.5 standard deviations below the control animals (27.0±5.9%).

EXAMPLE 2

Recombinantly produced human activin (produced as described in EP Publication No. 222,491, supra.) and recombinantly produced human inhibin (produced as described in EP Publication No. 222,491, supra) were used to test globin expression in erythroid cultures from cord blood of normal infants. Samples were prepared containing 100 nanograms/ml activin, 100 nanograms/ml inhibin and control. The results show that activin consistently enhanced fetal globin ($\gamma$-globin) production by 7 to 10% by autoradiography and densitrometry (5% by radioimmunoassay) and inhibin increased fetal globin production by 15 to 30% (autoradiography). Some growth inhibition was noted in the cultures containing inhibin. These results are equivalent to an enhancement by two to three times of the synthetic rate of fetal globin if induced in reticulocytes of sickle cell anemia patients.

The results on the erythrocyte cell cultures from an adult patient afflicted with $\beta$-thalassemia also showed that the $\alpha$:non-$\alpha$ chain ratio, which is a measure of extent of $\beta$ thalassemia, in $\beta$ thalassemia cultures, showed that treatment with recombinant activin at 100 nanograms/ml decreased the $\alpha$:non-$\alpha$ ratio by 25% and treatment with 100 nanograms/ml of recombinant inhibin decreased the $\alpha$:non-$\alpha$ ratio by 47% assayed by autoradiography and densitrometry. At these ratios, no transfusion would be required to a $\beta$-thalassemia patient.

EXAMPLE 3

To show the effect of activin/inhibin cord blood erythroid progenitors from cord blood from normal fetuses were cultured with and without a semipurified porcine follicular fluid containing both inhibin and activin, each in the amount of 100 ng/ml cell culture. In four out of five cultures, $\beta$-globin synthesis was decreased by a mean of 16.5% compared to untreated controls. Since FSH alone had no effect on globin synthesis in these cultures, the decrease in $\beta$-globin synthesis is attributed to activin and/or inhibin present in the follicular fluid.

What is claimed is:

1. A method for ameliorating $\beta$-globin disorders in a mammal comprising the step of introducing to said mammal periodically during its lifetime a compound selected from the group consisting of activin, inhibin, an inhibin chain, and derivatives and mixtures thereof, in an amount and frequency and duration of life sufficient to inhibit or reverse fetal $\gamma$ to $\beta$-globin switching.

2. A method according to claim 1 wherein said compound is selected from the group consisting of analogous mammalian forms of inhibin and activin, inhibin $\alpha$ chain, inhibin $\beta$ chain, prepro inhibin $\alpha$ chain, prepro inhibin $\beta$ chain, an amino acid sequence variant of inhibin $\alpha$ chain, an amino acid sequence variant of inhibin $\beta$ chain, pro inhibin $\alpha$ chain and pro inhibin $\beta$ chain.

3. A method according to claim 1 wherein said mammal is human and said disorder is sickle cell disease.

4. A method according to claim 1 wherein said mammal is human and said disorder is $\beta$-thalassemia.

5. A method according to claim 3 wherein said compound comprises human activin.

6. A method according to claim 3 wherein said compound comprises human inhibin.

7. A method according to claim 3 wherein said compound comprises porcine activin.

8. A method according to claim 3 wherein said compound comprises porcine inhibin.

9. A method for ameliorating $\beta$-globin disorders in a mammal comprising the step of administering follicle-stimulating hormone to said mammal in an amount and frequency effective to produce sufficient endogenous activin, inhibin, an inhibin chain, or a mixture thereof to inhibit or reverse fetal $\gamma$-globin to $\beta$-globin switching.

10. A method according to claim 3 wherein said compound is administered to a pregnant human prior to the thirty-second week of gestation of her fetus.

11. A method according to claim 9 wherein said hormone is administered to a pregnant human prior to the thirty-second week of gestation of her fetus.

12. A method for ameliorating $\beta$-globin disorders in a mammal comprising the step of introducing activin to the mammal, in an amount and at a frequency effective to inhibit or reverse fetal $\gamma$ globin to $\beta$-globin switching.

13. A method for ameliorating $\beta$-globin disorders in a mammal comprising the step of administering inhibin or an inhibin chain to the mammal, in an amount and at a frequency effective to inhibit or reverse fetal $\gamma$-globin to $\beta$-globin switching.

14. A method for ameliorating β-globin disorders in a mammal comprising the step of administering a mixture of activin and inhibin or an inhibin chain to the mammal, in an amount and at a frequency effective to inhibit or reverse fetal γ-globin to β-globin switching.

15. A method according to claim 12 wherein the introducing is conducted by administering the activin into the bloodstream of said mammal.

16. A method according to claim 13 wherein the introducing is conducted by administering the inhibin or inhibin chain in said mammal.

17. A method according to claim 14 wherein the introducing is conducted by administering said mixture into the bloodstream of said mammal.

18. A method according to claim 12 wherein the mammal is an adult.

19. A method according to claim 13 wherein the mammal is an adult.

20. A method according to claim 14 wherein the mammal is an adult.

21. A method according to claim 12 wherein the mammal is a fetus.

22. A method according to claim 13 wherein the mammal is a fetus.

23. A method according to claim 14 wherein the mammal is a fetus.

24. A method according to claim 12 wherein the mammal is an infant.

25. A method according to claim 13 wherein the mammal is an infant.

26. A method according to claim 14 wherein the mammal is an infant.

27. A method according to claim 24 wherein the infant is human and is less than four months old.

28. A method according to claim 25 wherein the infant is human and is less than four months old.

29. A method according to claim 26 wherein the infant is human and is less than four months old.

30. A method according to claim 12 wherein said activin is an analogous mammalian form of activin, a precursor of activin, or a complex of mature activin and its precursor.

31. A method according to claim 30 wherein the mammalian form of activin is porcine or human activin.

32. A method according to claim 13 wherein said inhibin or inhibin chain is selected from the group consisting of analogous mammalian forms of inhibin, inhibin α-chain, inhibin β-chain, prepro inhibin α-chain, prepro inhibin β-chain, pro inhibin α-chain, pro inhibin β-chain, the precursor of inhibin, and a complex of mature inhibin and its precursor.

33. A method according to claim 32 wherein said inhibin is porcine or human inhibin.

34. A method according to claim 12 wherein said mammal is human and said disorder is sickle cell anemia or a thalassemia.

35. A method according to claim 13 wherein said mammal is human and said disorder is sickle cell anemia or a thalassemia.

36. A method according to claim 14 wherein said mammal is human and said disorder is sickle cell anemia or a thalassemia.

37. A method according to claim 12 wherein said mammal is an adult human and said activin is administered at a dosage in the range of about 50 μg to 10 mg/kg body weight/day.

38. A method according to claim 13 wherein said mammal is an adult human and said inhibin or inhibin chain is administered at a dosage in the range of about 50 μg to 10 mg/kg body weight/day.

39. A method according to claim 14 wherein said mammal is an adult human and said activin and inhibin or inhibin chain are administered at dosages in the range of about 50 μg to 10 mg/kg body weight/day and 50 μg to 10 mg/kg body weight/day, respectively.

40. A method according to claim 12 further comprising administering to said mammal an effective amount of follicle-stimulating hormone.

41. A method according to claim 13 further comprising administering to said mammal an effective amount of follicle-stimulating hormone.

42. A method according to claim 14 further comprising administering to said mammal an effective amount of follicle-stimulating hormone.

43. A method according to claim 12 wherein the β-globin switching is monitored by adding to an in vitro cell culture from the mammal an effective amount of said activin to determine if additional treatment is needed.

44. A method according to claim 13 wherein the β-globin switching is monitored by adding to an in vitro cell culture from the mammal an effective amount of said inhibin or inhibin chain to determine if additional treatment is needed.

45. A method according to claim 14 wherein the β-globin switching is monitored by adding to an in vitro cell culture from the mammal an effective amount of said mixture to determine if additional treatment is needed.

46. A method according to claim 36 wherein said mammal is an adult human and said hormone is administered at a dosage in the range of 10 to 500 micrograms/kg body weight/day.

47. A method for diagnosing sickle cell disease in a mammal comprising the steps of culturing a biological sample from the mammal with an effective amount of activin and measuring the decrease in β-globin synthesis of the sample as compared to a control sample cultured in the absence of the activin.

48. A method for diagnosing sickle cell disease in a mammal comprising the steps of culturing a biological sample from the mammal with an effective amount of inhibin or an inhibin chain and measuring the decrease in β-globin synthesis of the sample as compared to a control sample cultured in the absence of the activin.

49. A method for diagnosing sickle cell disease in a mammal comprising the steps of culturing a biological sample from the mammal with an effective amount of a mixture of inhibin or an inhibin chain and activin and measuring the decrease in β-globin synthesis of the sample as compared to a control sample cultured in the absence of the mixture.

* * * * *